United States Patent [19]
Cochran et al.

[11] Patent Number: 5,919,485
[45] Date of Patent: Jul. 6, 1999

[54] ORAL 2-METHYL-THIENO-BENZODIAZEPINE FORMULATION

[75] Inventors: George Randall Cochran; Tommy Clifford Morris, both of Indianapolis, Ind.

[73] Assignee: Eli Lilly and Company, Indianapolis, Ind.

[21] Appl. No.: 08/716,922

[22] Filed: Sep. 20, 1996

Related U.S. Application Data

[63] Continuation-in-part of application No. 08/410,465, Mar. 24, 1995, abandoned.

[51] Int. Cl.$^6$ ...................................................... A61K 9/36
[52] U.S. Cl. ........................ 424/480; 424/464; 424/470; 424/461; 424/494; 424/495
[58] Field of Search ..................................... 424/480, 464; 514/220

[56] References Cited

U.S. PATENT DOCUMENTS

| | | | |
|---|---|---|---|
| 4,115,568 | 9/1978 | Chakrabarti et al. | 424/250 |
| 5,229,382 | 7/1993 | Chakrabarti et al. | 514/220 |
| 5,457,101 | 10/1995 | Greenwood et al. | 514/220 |

FOREIGN PATENT DOCUMENTS 582 368 A1   5/1993   European Pat. Off. .

*Primary Examiner*—Thurman K. Page
*Assistant Examiner*—William E. Benston, Jr.
*Attorney, Agent, or Firm*—Arleen Palmberg; MaCharri Vorndran-Jones; David E. Boone

[57] ABSTRACT

The invention provides a pharmaceutically acceptable solid oral formulation of olanzapine and a process for making such formulation.

19 Claims, No Drawings

ORAL 2-METHYL-THIENO-BENZODIAZEPINE FORMULATION

This application is a continuation-in-part of U.S. Ser. No. 08/410,465 filed on Mar. 24, 1995 which has been abandoned.

BACKGROUND OF THE INVENTION

This invention provides an improved pharmaceutically elegant tablet formulation of 2-methyl-4-(4-methyl-1-piperazinyl)-10H-thieno[2,3-b][1,5]benzodiazepine, hereinafter referred to as olanzapine, and processes for the preparation thereof.

Olanzapine has shown great promise in the treatment of psychotic patients and is currently being evaluated for that purpose. Certain tablet formulations of olanzapine are known, as described in U.S. Pat. No. 5,229,382. However, improved oral formulations were desired in light of the moisture sensitive, metastable nature of olanzapine, the tendency of olanzapine to undesirably discolor in the known tablet formulation, and due to the surprisingly potent nature of olanzapine.

The presently claimed invention provides a pharmaceutically elegant solid oral formulation comprising olanzapine as an active ingredient intimately mixed with a bulking agent, binder, disintegrant, a dry binder to provide friability, and a lubricant; wherein such solid oral formulation is coated with polymer selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmethacrylate copolymer, methylcellulose, and ethylcellulose.

It is particularly preferred that the polymer coat does not contain polyethylene glycol.

Further, the invention provides a method for preparing pharmaceutically elegant, stable solid oral olanzapine formulations having a polymer coat selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmethacrylate copolymer, methylcellulose, and ethylcellulose, comprised of using a high shear aqueous wet granulation with fluid bed drying process.

DETAILED DESCRIPTION OF THE INVENTION

Olanzapine, a potent compound showing promising activity for use in treating psychotic patients, tends to be metastable, undergo pharmaceutically undesired discoloration, and demands care to assure homogeniety of the finished solid formulation.

Applicants have discovered that olanzapine undergoes undesirable discoloration when contacted with certain excipients including powder blends. Further, the discoloration is exacerbated by ambient air conditions, at elevated temperatures, and by moist environments.

Although the discoloration phenomenon does not produce an increase in the number of total related substances, the browning and mottling appearance is not generally considered pharmaceutically acceptable for commercial purposes. Further, the discoloration is particularly disturbing when a tablet formulation is administered to a psychotic patient, which patient may be especially troubled by the changing appearance of their medication.

Applicants have discovered that coating the solid oral formulation with a polymer selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmethacrylate copolymer, methylcellulose, and ethylcellulose as a coating or subcoating provides a uniform, physical stability and effectively prevents the undesired discoloration phenomenon in the formulation. The formulation is most preferredly in a tablet form; however, granule formulation and the like are desired as well.

Most preferred polymer coats are hydroxypropyl methyl cellulose, hydroxypropylcellulose, methylcellulose, and ethylcellulose. An especially preferred polymer coat is hydroxypropyl methylcellulose.

It is especially preferred that the formulation contain the most stable anhydrous form of olanzapine, referred to herein as Form II; however, other forms of olanzapine are contemplated. Form II has a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper K$_\alpha$ radiation source of wavelength, $\lambda$=1·541 Å.

The formulation of the invention preferredly contains substantially pure Form II as the active ingredient.

As used herein "substantially pure" refers to Form II associated with less than about 5% undesired polymorphic form of olanzapine (herein referred to as "Undesired Form"), preferably less than about 2% Undesired Form, and more preferably less than about 1% Undesired Form. Further, "substantially pure" Form II will contain less than about 0.5% related substances, wherein "related substances" refers to undesired chemical impurities or residual solvent or water. In particular, "substantially pure" Form II preferably contain less than about 0.05% content of acetonitrile, more preferably, less than about 0.005% content of acetonitrile. Additionally, Form II preferredly contain less than 0.5% of associated water.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

Form II is the most stable anhydrous form of olanzapine known and is therefore important for the commercial development of pharmaceutically elegant formulations. Olanzapine may form an undesired crystal form in the presence of certain solvents and excipients, therefore, in making the compositions of the invention it is most desired to prepare the formulation using a method which does not require dissolution of the olanzapine substance. The desired Form II can be converted to less desirable polymorphic forms by contact with methylene chloride, for example. Additionally, for example, polyethylene glycol contact with the olanzapine substance produces undesired discoloration, particularly under moist conditions.

Applicants believe that a dry blend direct compression process or dry granulated processes for preparing solid oral formulations create a greater chance that poor dose uniformity will occur. In light of the potent nature of olanzapine, consistent dose uniformity is imperitive. In accordance with this invention, Applicants have discovered that a high shear aqueous wet granulation with fluid bed drying is the most effective method for preparing pharmaceutically elegant, stable, oral olanzapine formulations.

Uncoated tablets stored at ambient conditions (approximately 23° C. and 40% relative humidity) in amber, high density polyethylene bottles do not show signs of discoloration after 24 months; however, if the bottle is opened such that the tablets are exposed to open air ambient conditions then discoloration occurs within 5 days.

A new solid oral formulation was prepared that used a hydroxypropropyl methylcellulose subcoating and a white color coating. The new formulation did not discolor after 90 days of open dish storage at 40° C., 60° C., 40° C./75 %RH, ambient temperature with 75% RH, or at ambient temperature with 85% RH. The hydroxypropyl methylcellulose coating which is free of polyethylene glycol is much preferred to ensure that discoloration does not occur on the tablet surface. It provides an effective barrier between the white color coat which provides an acceptable medium for imprinting and color dressing of the product. The hydroxypropylmethylcellulose coating provides sufficient barrier to prevent discoloration attributable to the polyethylene glycol in the white color coat. Alternative white film coat formulas containing alternative plasticizers were evaluated; however, none were able to prevent discoloration in all test conditions after 90 days of storage. Therefore, the hydroxypropyl methylcellulose coat or subcoating is a surprising and important component of pharmaceutically elegant solid oral formulations of olanzapine.

A diluent or bulking agent should be selected to provide an increase in tablet size. The artisan can utilize known methods to select a bulking agent which provides hardness, friability, and disintegration time that is satisfactory for pharmaceutical usage. The bulking agent should be selected to provide a tablet that has characterstics desired by the patient as well as comply with applicable regulatory guidelines.

One especially preferred diluent or bulking agent is lactose. Various forms of lactose are appropriate for such formulations including anhydrous, hydrous, and spray dried forms. The most desired form of lactose can be selected based on desired dissolution, content uniformity, hardness, friability, and disintegration time. The skilled artisan is aware of the regulatory requirements for hardness, friability, and disintegration time and can adjust the diluent or bulking agents using known techniques to achieve the desired physical characteristics.

The formulation should include a binder for use in the granulation step. The artisan can choose an appropriate binder based on the acceptable viscosity, and desired hydration. Hydroxypropyl cellulose is especially preferred for use as a binder in the granulation step. The hydroxypropyl cellulose may vary in particle size. Fine grade hydroxypropyl cellulose is especially preferred for most claimed formulations.

The desired formulation includes a disintegrant for use in the granulation as well as in the running powders to facilitate the disintegration process. There are a variety of grades available, and the grade may be selected based on the acceptable batch variability. A particularly prefered disintegrant is crospovidone. A fine grade of crospovidone provides particularly desirable consistency between batches.

The artisan may choose appropriate dry binders using known methods. Such binders should be selected to assure that satisfactory friability is attained. Most preferably, dry binder is microcrystalline cellulose; however, other appropriate dry binders may be selected. Such microcrystalline cellulose may be in a granular form.

The artisan can choose an appropriate lubricant to prevent sticking and picking of the tablets to the compression tooling. One preferred lubricant is magnesium stearate.

The artisan can readily choose other appropriate aqueous dispersion film coats (color mix) for application over the hydroxypropyl methylcellulose layer. Typically, the color mixture is a dry blend of ingredients which may be dispersed in water and used as an aqueous dispersion to film coat solid formulations. One example of a typical color mixture is comprised of hydroxypropyl methylcellulose, polyethylene glycol, polysorbate 80, and titianium dioxide.

A variety of edible inks known to the artisan are appropriate for imprinting the finished formulation. For example, one typical edible ink is comprised of shellac, ethyl alcohol, isopropyl alcohol, n-butyl alcohol, propylene glycol, ammonium hydroxide, and FD&C Blue.

The solid formulation is most preferably subcoated with hydroxypropyl methylcellulose, coated with a color coat, and imprinted with an edible ink. The solid formulation may be polished using standard methods such as carnauba wax polishing, if desired.

Olanzapine is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of central nervous system disorders, a dose range of from 1 to 30 mg, preferably 1 to 20 mg per day is suitable. Radiolabelled Form II 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg olanzapine as an active ingedient, wherein such solid oral formulation is coated with hydroxypropyl methylcellulose. Especially preferred is an oral formulation comprising from 1 to 20 mg of anhydrous Form II olanzapine as an effective amount of the active ingredient, provided that such solid oral formulation is coated with hydroxypropyl methylcellulose.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

A study of the hydroxypropyl methylcellulose subcoated tablets in an amber colored bottle having a desiccant pack stored at harsh, 40° C./75% RH conditions for six months showed pharmaceutically acceptable stability with a 0.4% to about 1.2% increase in total related substances.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. It is most desirable to prepare a rapidly dissolving formulation comprising substantially pure crystalline Form II. Such substantially pure crystalline Form II olanzapine may be prepared using the techniques described herein by the Preparation section herein infra.

Compound characterization methods include, for example, x-ray powder pattern analysis, thermogravimetric analysis (TGA), differential scanning calorimetery (DSC), titrametric analysis for water, and $H^1$-NMR analysis for solvent content.

The formulations were studied to assure that the Form II polymorph was substantially pure using $^{13}C$ Cross polarization/magic angle spinning (CP/MAS) NMR. Spectra were obtained using a Varian Unity 400 MHz spectrometer operating at a carbon frequency of 100.577 MHz and equipped with a complete solids accessory and Varian 5 mm or 7 mm VT CP/MAS probes. Measurement conditions were optimized for Olanzapine Form II and were as follows: 90° proton r.f. pulse 4.5 ms, contact time 1.1 ms, pulse repetition time 5 s, MAS frequency 7.0 kHz, spectral width 50 kHz, and acquisition time 50 ms. Chemical shifts were referenced to the $CH_3$ of hexamethylbenzene (d=17.3 ppm) by sample replacement. It was determined that the substantially pure Form II polymorph is retained throughout the formulation process claimed herein. Therefore, the formulations of this invention provide substantially pure Form II olanzapine polymorph in a pharmaceutically elegant formulation without producing undesired polymorphic transformation.

The following examples are provided for purposes of illustration and are not to be construed as limiting the scope of the claimed invention.

Preparation 1

Technical Grade Olanzapine

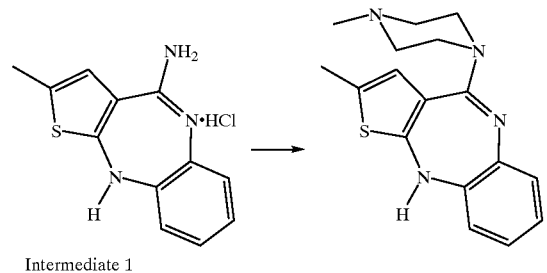

Intermediate 1

In a suitable three neck flask the following was added:

Dimethyl sulfoxide (analytical): 6 volumes

Intermediate 1: 75 g

N-Methylpiperazine (reagent): 6 equivalents

Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until <5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

Preparation 2

Form II

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency $\geq 97\%$, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg olanzapine, respectively, per tablet:

1 mg olanzapine per tablet:

| Names of Ingredients | Quantity (mg/tablet) |
| --- | --- |
| Active Ingredient | |
| Olanzapine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoating | |
| Hydroxypropyl Methylcellulose Coating | 1.70 |
| Color Mixture White Polishing | 3.47 |
| Carnauba Wax Imprinting | trace |
| Edible Blue Ink | trace |

Olanzapine 2.5 mg Tablets

| Names of Ingredients | Quantity (mg/tablet) |
| --- | --- |
| Active Ingredient | |
| Olanzapine | 2.5 |
| Other Ingredients | |
| Lactose | 102.15 |
| Hydroxypropyl Cellulose | 5.20 |
| Crospovidone | 5.50 |
| Microcrystalline Cellulose | 13.00 |
| Magnesium Stearate | 0.65 |
| Subcoating | |
| Hydroxypropyl Methylcellulose Coating | 2.60 |
| Color Mixture White Polishing | 5.30 |
| Carnauba Wax Imprinting | trace |
| Edible Blue Ink | trace |

Olanzapine 5.0 mg Tablets

| Names of Ingredients | Quantity (mg/tablet) |
| --- | --- |
| Active Ingredient | |
| Olanzapine | 5.00 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |
| Subcoating | |
| Hydroxypropyl Methylcellulose Coating | 4.00 |
| Color Mixture White Polishing | 8.16 |
| Carnauba Wax Imprinting | trace |
| Edible Blue Ink | trace |

Olanzapine 7.5 mg Tablets

| Names of Ingredients | Quantity (mg/tablet) |
| --- | --- |
| Active Ingredient | |
| Olanzapine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating | |
| Hydroxypropyl Methylcellulose Coating | 6.00 |
| Color Mixture White Polishing | 12.24 |
| Carnauba Wax Imprinting | trace |
| Edible Blue Ink | trace |

Olanzapine 10.0 mg Tablets

| Names of Ingredients | Quantity (mg/tablet) |
| --- | --- |
| Active Ingredient | |
| Olanzapine | 10.00 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating | |
| Hydroxypropyl Methylcellulose Coating | 8.00 |
| Color Mixture White Polishing | 16.32 |
| Carnauba Wax Imprinting | trace |
| Edible Blue Ink | trace |

We claim:

1. A solid oral formulation comprising olanzapine, wherein the formulation is coated with a polymer selected from hydroxypropyl methyl cellulose, hydroxyethyl cellulose, methyl hydroxyethyl cellulose, sodium carboxymethyl cellulose, hydroxypropyl cellulose, polyvinylpyrrolidone, dimethylaminoethyl methacrylate, methyl acrylate acid ester copolymer, ethyl acrylate-methyl methacrylate copolymer, methyl cellulose, and ethyl cellulose.

2. The formulation of claim 1 wherein the polymer is hydroxypropyl methyl cellulose, hydroxypropyl cellulose, methyl cellulose, or ethyl cellulose.

3. A formulation of claim 2 wherein the polymer is hydroxypropyl methyl cellulose.

4. A formulation of claim 1 wherein the coating is free of propylene glycol.

5. A formulation of claim 4 wherein the bulking agent in the formulation is lactose.

6. A formulation of claim 4 wherein the binder in the formulation is hydroxypropyl cellulose and the disintegrant is crospovidone.

7. A formulation of claim 1 wherein the dry binder in the formulation is microcrystalline cellulose.

8. A formulation of claim 1 wherein the lubricant in the formulation is magnesium stearate.

9. A formulation of claim 3 wherein the hydroxypropyl methyl cellulose coating is further coated with an aqueous dispersion film coat.

10. A formulation of claim 9 wherein the solid formulation is imprinted using an edible ink.

11. A formulation of claim 9 wherein the formulation comprises from about 1 to about 3% w/w olanzapine; from about 69.5 to about 87.5% w/w lactose; from about 3.5 to about 4.5% w/w hydroxypropyl cellulose; from about 4 to about 6% w/w crospovidone; from about 9 to about 11% w/w microcrystalline cellulose; and from about 0.25 to 1% w/w magnesium stearate.

12. A formulation of claim 1 wherein the solid formulation is a tablet.

13. A formulation of claim 12 wherein each tablet provides a 1, 2.5, 5, 7.5, 10, 15, or 20 mg dose of olanzapine.

14. A formulation of claim 1 wherein the solid formulation is in the form of granules.

15. A solid formulation of claim 1 wherein the formulation is for use in treating a condition selected from psychosis, schizophrenia, a schizophriform disorder, mild anxiety, a gastrointestinal disorder, and acute mania.

16. A formulation of claim 12 wherein each tablet provides a 25 mg dose of olanzapine.

17. The formulation of claim 1 wherein the olanzapine is substantially in the form of the Form II polymorph.

18. A process for preparing a formulation of claim 1 comprising high shear aqueous wet granulation with fluid bed drying.

19. The process of claim 18 wherein the olanzapine is substantially in the form of the Form II polymorph.

\* \* \* \* \*